(12) United States Patent
Shay

(10) Patent No.: US 8,585,659 B2
(45) Date of Patent: Nov. 19, 2013

(54) PIERCING DEVICE FOR DRUG DELIVERY SYSTEMS

(75) Inventor: Christopher D. Shay, Horseshoe Bay, TX (US)

(73) Assignee: Mystic Pharmaceuticals, Inc., Cedar Park, TX (US)

( * ) Notice: Subject to any disclaimer, the term of this patent is extended or adjusted under 35 U.S.C. 154(b) by 9 days.

(21) Appl. No.: 13/149,584

(22) Filed: May 31, 2011

(65) Prior Publication Data

US 2012/0310176 A1   Dec. 6, 2012

(51) Int. Cl.
*A61M 5/00* (2006.01)

(52) U.S. Cl.
USPC ............. 604/244; 604/58; 604/181; 604/185; 206/532; 222/541.1; 128/200.14

(58) Field of Classification Search
USPC .................. 604/58, 181, 185, 201, 204, 244; 128/200.14, 203.31; 206/528, 532; 222/541.2
See application file for complete search history.

(56) References Cited

U.S. PATENT DOCUMENTS

| | | | |
|---|---|---|---|
| 2,769,443 | A | 11/1956 | Dunmire |
| 4,627,432 | A | 12/1986 | Newell et al. |
| 4,684,366 | A | 8/1987 | Denny et al. |
| 4,798,288 | A | 1/1989 | Holzner |
| 4,852,551 | A | 8/1989 | Opie et al. |
| 5,154,710 | A | 10/1992 | Williams |
| 5,215,221 | A | 6/1993 | Dirksing |
| 5,616,128 | A | 4/1997 | Meyer |
| 6,105,761 | A | 8/2000 | Peuker et al. |
| 6,116,238 | A | 9/2000 | Jackson et al. |
| 6,708,846 | B1 | 3/2004 | Fuchs et al. |
| 7,097,075 | B2 | 8/2006 | Peuker et al. |
| 7,143,765 | B2 | 12/2006 | Asking et al. |
| 7,669,597 | B2 | 3/2010 | Sullivan et al. |
| 7,963,089 | B2 | 6/2011 | Nelson et al. |
| 8,047,204 | B2 | 11/2011 | Sullivan et al. |
| 2004/0215133 | A1 | 10/2004 | Weber et al. |
| 2005/0238708 | A1 | 10/2005 | Jones et al. |
| 2007/0051362 | A1 | 3/2007 | Sullivan et al. |
| 2008/0123465 | A1 | 5/2008 | Heusser et al. |
| 2008/0177246 | A1 | 7/2008 | Sullivan et al. |
| 2008/0283439 | A1* | 11/2008 | Sullivan et al. ............... 206/531 |
| 2010/0331765 | A1 | 12/2010 | Sullivan et al. |
| 2011/0247305 | A1 | 10/2011 | Nelson |
| 2011/0277763 | A1 | 11/2011 | Sullivan et al. |

FOREIGN PATENT DOCUMENTS

| | | |
|---|---|---|
| WO | WO 94/20408 | 9/2004 |
| WO | WO 2005/032998 | 4/2005 |
| WO | WO 2005/102058 | 11/2005 |
| WO | WO 2008/086413 | 7/2008 |
| WO | WO 2008/144439 | 11/2008 |
| WO | WO 2009/036422 | 3/2009 |

OTHER PUBLICATIONS

PCT/US2012/040006, International Search Report, Sep. 7, 2012.

* cited by examiner

*Primary Examiner* — Emily Schmidt
(74) *Attorney, Agent, or Firm* — Vinson & Elkins LLP

(57) ABSTRACT

Devices for delivery of medical compositions in either liquid or powder form include a piercing device for piercing a flexible sheet material in which when contained in a flexible blister dosage form, the piercing device serves as a delivery channel for compositions contained in the blister. The device is configured to reduce or inhibit puncture flap interference with the delivered spray or mist by forming a substantial non-contact drape in the material prior to puncture.

20 Claims, 9 Drawing Sheets

PIERCING DEVICE FOR DRUG DELIVERY SYSTEMS

CROSS-REFERENCE TO RELATED APPLICATIONS

N/A

STATEMENT REGARDING FEDERALLY SPONSORED RESEARCH OR DEVELOPMENT

N/A

BACKGROUND OF THE INVENTION

There is a growing number of drugs and vaccines for which the most effective, or most convenient method of administration is by delivery of a spray or mist. A variety of devices are known for delivering a controlled amount of a pharmaceutical preparation in a spray, stream or mist to the nose, eye, ear, lungs, oral mucosal membranes, such as in the buccal region, or throat of a user, or for topical delivery of an active agent. Various devices for systemic or topical delivery of a liquid or even a powdered formulation include a measured amount of a pharmaceutical composition contained in a crushable ampoule, blister or other dosage form that is forced against a penetrating device during use, to pierce the dosage form and release the contents.

The effectiveness of this type of dosage depends on the ability to deliver a precisely measured amount of active agent through a small opening with enough force and with control of the spray, stream or mist geometry to ensure that the correct amount of active agent reaches the desired target. This is of particular importance as more drugs and vaccines are being delivered to the eye, oral mucosal membranes, nasal mucosa or to the lungs through the nasal passages. It is a further advantage if the active agents can be stored and delivered from the same dosage form without the risk of contamination prior to delivery.

SUMMARY

The present disclosure provides drug, biologics or pharmaceutical dosage forms for use in delivery devices that deliver a stream, drops, particles, spray or mist in a desired volume and spray geometry to a human or non-human animal. The dosage forms can be used, for example, to deliver a measured dose of a pharmaceutical, biologic or medical composition to the nasal passages, to the eye, to the mouth, into the ear, into the lungs, into the throat, or to a topical location of a user. In preferred embodiments a predetermined quantity of a pharmaceutical or medical composition comprising a fluid or a solid such as a powder or a lyophilized agent is contained in, or produced in an ampoule or blister dosage form that is crushed by a plunger with sufficient force to drive the dosage form against a piercing mechanism, piercing the dosage form and forcing the liquid or solid contents from the dosage form and through a delivery channel into a spray to be directed to the recipient. A predetermined quantity refers, in most instances, to a single dose of medication or a pharmaceutical, biologic or medical composition, and in certain embodiments to a prescribed dose. A predetermined quantity of fluid or solid dose may also be a partial dose when delivery of a dose is administered in two or more spray events.

Any pharmaceutical agent that is deliverable in a powder, lyophilized, or liquid form is contemplated in the present disclosure, including but not limited to antibiotics, antipyretics, anti-inflammatories, biologics, vitamins, co-factors, enzymes, inhibitors, activators, nutrients, vaccines including DNA based killed or live virus or microorganisms, nucleic acids, proteins, peptides, antibodies, peptide mimetics, or other agents or pharmaceutical compositions known in the art. The pharmaceutical compositions are in the form of a liquid, a powder, a lyophilized agent, or any combination thereof, and include one or more active agents, which may be combined or mixed with pharmaceutically acceptable carriers, solvents, diluents, preservatives, surfactants, salts, adjuvants, viscosity agents, buffers, chelators, or other ingredients known to those in the art as needed.

In preferred embodiments when the dosages are intended to be delivered or administered to a human subject, the preferred agents, e.g., matrix materials, therapeutic agent, active agent, surfactant, and functional excipients of the present disclosure are pharmaceutically acceptable materials. As used herein, "pharmaceutically acceptable carrier" or "pharmaceutically acceptable materials" includes any and all solvents, dispersion media, coatings, antibacterial and antifungal agents, isotonic and absorption delaying agents, absorption enhancing agents and the like. The use of such media and agents for pharmaceutically active agents is well known in the art. Except insofar as any conventional media or agent is incompatible with the active agent, its use in the therapeutic compositions is contemplated. Supplementary active agents can also be incorporated into the compositions. The phrase "pharmaceutically acceptable" also refers to molecular entities and compositions that do not produce an allergic or similar untoward reaction when administered to a human or animal.

The present disclosure arose, at least in part from the discovery that when delivering a spray from a crushable blister through an internal piercing mechanism, a puncture flap can be formed in the film that at least partially covers the central delivery channel and can interfere with the spray, causing a significant decrease in the effectively delivered dose.

The present invention can be described in certain embodiments as a piercing device for delivering a predetermined quantity of medicament contained in a crushable blister into a spray or mist. The device is preferable contained in a dome or modified dome shaped blister as an internal piercing mechanism such that, when the blister is crushed by a ram or plunger, for example the internal piercing mechanism is forced against the sealed side of the blister and penetrates the seal and the contents of the blister are forced out through the piercing device in a spray pattern.

The device can include a base; a substantially hollow, elongated member extending from the base forming a shoulder region opposite the base end of the elongated member; an internal delivery channel extending from the base to the tip and formed by the hollow interior of the elongated member. The main body of the piercing device or the elongated member can be elliptical or oval shaped in cross section. The member can taper slightly toward the tip so long as the circumference at the shoulder region is large relative to the tip of the device. The tip of the device is a smaller annular elongate member projecting from the shoulder region of the elongated member wherein the circumference of the annular elongate member is less than the circumference of the shoulder region and ending in a piercing tip opposite the shoulder end wherein the tip is configured to form a non-contact drape region on opposites sides of the tip when pressed into a flexible material. The tip is thus shaped relative to the shoulder region such that a tightly stretched material will touch the tip and the shoulder but will not contact the elongated body of the tip region. The internal channel passes through the tip and is open to form a discharge port in fluid communication with the internal delivery channel. The device also includes one or more inlet openings on the base end and one or more conduits providing fluid communication between the one or more inlet ports and the internal channel.

The configuration of preferred embodiments can be better understood by referring to the drawings where it can be seen that the piercing device includes a projected tip for piercing a film and that the tip is of smaller diameter and can be described as a nipple.

In certain embodiments the piercing device can include structural features on the surface of the internal delivery channel to affect the spray pattern and droplet size of a fluid or powder forced through the piercing device during use. The structural features are designed to be compatible with the particular medicament to be delivered and vary depending on the viscosity, delivery site and other factors specific to the particular medicament. As such the structures can include, but are not limited to steps, flutes, ribs, or a combination thereof. In addition to the internal structures, the delivery channel can include bends and turns to produce turbulence in the fluid as it travels through the delivery path. Such bends can be right angles, or 90° turns, or they can be angles from about 45° to about 135°. The fluid paths in the base can also be arranged to produce a vortex in the fluid or powder as it is forced through the delivery channel.

The disclosure can also be described as a piercing device in which the elongated member has an elliptical cross-section; wherein the projected piercing tip is concentric with the elliptical member, the major axis of the ellipse is from about 1 to 1.5 times the minor axis and the diameter of the projected tip is less than 50% of the major axis of the ellipse where the tip projects from the shoulder region.

In certain preferred embodiments the disclosure is a dosage from containing a piercing device as described herein. The dosage form can be a crushable blister or ampoule containing a liquid or powder medical composition. Such dosage forms are know for use in delivery systems in which a ram or piston is forced against the dosage form, forcing the contents out through a delivery channel.

The disclosure can also be described in certain embodiments as an internally pierced dosage form including a substantially dome shaped, flexible blister; a substantially round pierceable surface sealed to the base of the dome-shaped blister; and an internal chamber; wherein the internal chamber contains a piercing device and a medical composition and wherein the piercing device comprises: a base; a substantially hollow, elongated member extending from the base forming a shoulder region opposite the base end of the elongated member; an internal delivery channel extending from the base to the tip and formed by the hollow interior of the elongated member; an annular elongate member projecting from the shoulder region of the elongated member wherein the circumference of the annular elongate member is less than the circumference of the shoulder region and ending in a piercing tip opposite the shoulder end wherein the tip is configured to form a non-contact drape region on opposites sides of the tip when pressed into a flexible material; and further forming a discharge port in fluid communication with the internal delivery channel; and one or more inlet openings on the base end and one or more conduits providing fluid communication between the one or more inlet ports and the internal channel.

The dosage form can also be described wherein the piercing device further includes structural features on the surface of the internal delivery channel to affect the spray pattern and droplet size of a fluid forced through the piercing device during use, including but not limited to steps, flutes, ribs, or a combination thereof. The internal channel can also provide one or more bends or turns to impart turbulence or a vortex to the fluid during delivery.

The piercing device can also include an elongated member that has an elliptical cross-section; wherein the projected piercing tip is concentric with the elliptical member, the major axis of the ellipse is from about 1 to 1.5 times the minor axis and the diameter of the projected tip is less than 50% of the major axis of the ellipse where the tip projects from the shoulder region. The piercing device is disposed inside the dosage form and can be attached by the base to the dome shaped blister with the piercing tip is proximate the piercable surface.

In certain embodiments, therefore, the disclosure may also be described as a piercing nozzle for dispensing a fluid or solid composition from a dosage form with a particular volume, in a controlled spray pattern and droplet size. The nozzle includes an oval shaped elongate member with an inlet end and a discharge end, an internal channel connecting the inlet end and the discharge end in fluid communication, one or more inlet openings in the inlet end, a nipple shaped tip forming a discharge opening in the discharge end, and features on the internal chamber surface to control the spray pattern and droplet size of a fluid forced through the nozzle. The inlet ports are designed to provide a fluid path into the internal channel that includes one or more right angle turns. The inlet ports can also be designed to produce a vortex in the liquid or solid composition as it is forced through the ports. Features in the internal channel can also include, but are not limited to, steps, flutes, ribs, constrictions, contours, and related structures to produce the desired droplet size and spray geometry. In certain embodiments, the piercing tip may be on the discharge end of the elongated member, or on the inlet end. The piercing nozzle can be contained in a dosage form. The disclosure includes, therefore, a dosage form that comprises the piercing nozzle and a pharmaceutical composition.

In certain embodiments the present disclosure can be described as an internally pierced dosage form that includes a substantially dome shaped, flexible blister, a substantially round pierceable surface sealed to the base of the dome-shaped blister, and an internal chamber containing a piercing nozzle as described herein and a liquid composition. In certain embodiments the piercing nozzle includes a base and a piercing end, and wherein the base is attached to the dome shaped blister and the piercing end is proximate the piercable surface and wherein the piercer is oval shaped with a nipple shaped piercing tip.

It is contemplated that any embodiment discussed in this specification can be implemented with respect to any process, device, or composition of the invention, and vice versa. The term "about" as used herein is defined as being close to as understood by one of ordinary skill in the art, and in one non-limiting embodiment the terms are defined to be within 10%, within 5%, within 1%, or within 0.5%. The term "substantially" and its variations as used herein are defined as being largely but not necessarily wholly what is specified as understood by one of ordinary skill in the art, and in one non-limiting embodiment substantially refers to ranges within 10%, within 5%, within 1%, or within 0.5%. The use of the word "a" or "an" when used in conjunction with the term "comprising" in the claims and/or the specification may mean "one," but it is also consistent with the meaning of "one or more," "at least one," and "one or more than one."

It is to be understood that each of the variously stated ranges herein is intended to be continuous so as to include each numerical parameter between the stated minimum and maximum value of each range. It is to be further understood that, while not intending to limit the applicability of the doctrine of equivalents to the scope of the claims, each numerical parameter should at least be construed in a manner consistent with the reported number of significant digits for each numerical parameter and by applying ordinary rounding techniques. It is to be even further understood that, while not intending to limit the applicability of the doctrine of equivalents to the scope of the claims, even though a number may be contained within a numerical range wherein at least one of the minimum and maximum numbers of the range is preceded by the word "about," each numerical value contained within the range may or may not be preceded by the word "about." For Example, a range of about 1 to about 4 includes about 1, 1, about 2, 2, about 3, 3, about 4, and 4.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used in this example and throughout the specification, unless the context indicates otherwise, these terms are defined as follows.

First fissure: The primary and immediate initial split in the lidstock material that precedes the actual puncture.

Distal end: On any extremity, the furthest point from the proximal end, i.e. for the piercing mechanism, the point furthest from the piercer base.

The Drape: During puncture, the lidstock material that is in between the piercer tip and the main body of lidstock material.

Non-contact Drape: That portion of the drape that does not contact the piercer.

In certain embodiments the unit dosage forms of the present disclosure are blisters that can be manufactured as described in US Application Publication No. 20090071108, incorporated in its entirety herein by reference. The manufacturing processes for shaping articles for unit-dose packaging with at least one formed recess (e.g., a blister), in particular for unit-dose packaging of pharmaceutical dosage forms, can include a step of drawing the film material (e.g., metal-plastic foil) with one or more plungers to form a primary contour, the contour having a depth of at least 100% and up to 150% of the depth of the formed recess. A second stage involves shaping the primary contour with one or more plunger(s) to the desired formed recess, with a depth that is less than the depth of the primary contour, while substantially maintaining the surface area of the primary contour formed in the first stage. The formed recess may be formed using warm-forming or cold-forming techniques.

The disclosed devices may be described in certain embodiments as devices for dispensing a predetermined quantity of fluid into the nasal passage of a user, or into the eye or ear of a user, in which the predetermined quantity of fluid is contained in, or produced in an ampoule or blister dosage form that is crushed by a plunger with sufficient force to drive the dosage form against a piercing mechanism, piercing the dosage form and forcing the liquid contents from the dosage form and through a delivery channel into a spray to be directed to the user. A predetermined quantity refers, in most instances to a single dose of medication or a pharmaceutical or medical composition, and in certain embodiments to a prescribed dose. A predetermined quantity of fluid may also be a partial dose when delivery of a dose is administered in two or more spray events. Any pharmaceutical agent that is deliverable in a powder or liquid from is contemplated in the present disclosure, including but not limited to antibiotics, antipyretics, anti-inflammatories, biologics, vitamins, co-factors, enzymes, inhibitors, activators, nutrients, aptamers, thio-aptamers, vaccines including killed or live virus or microorganisms, nucleic acids, proteins, peptides, antibodies, peptide mimetics, or other agents known in the art. The medical compositions are in the form of a liquid, a powder, or a combination of liquid and powder and include one or more active agents and combinations of pharmaceutically acceptable carriers, solvents, diluents, preservatives, surfactants, salts, adjuvants, viscosity agents, buffers, chelators, or other ingredients known to those in the art as needed.

The volume of droplets or particles dispensed from the devices will depend on the site of dispensing as well as the content and viscosity of the medication to be delivered. In certain embodiments droplet to be delivered to the eye would be from 1 µl to 50 µl, or more typically from 7 µl to 50 µl. Dosage for nasal administration are typically from 75 µl to 500 µl and dosages for oral or topical cutaneous administration can be larger, as much as 1000 µl or more. The volume and size of droplets or particles released by a device can be adjusted to maximize the therapeutic benefit of the dispersed substance. The volume of substance dispensed depends on the size of the compartment containing the substance, the unit dosage form blister, the piercer, the fill level, the degree to which the dosage form is compressed by the device and other variables in the construction of the devices, as well as characteristics of the substance dispersed, which are well understood by those skilled in the art. These variables can be appropriately dimensioned to achieve dispersal of a desired volume or droplet size of liquid or particle size of substance to the user. One of skill in the art understands that residual liquid or other substance after dispersal is taken into account when formulating the appropriate parameters for dispersing the desired dosage volume.

An advantage of the devices and unit dosage form designs set forth herein is that the sterility of the administered substance is maintained until the moment of use. Maintaining sterility until the moment of use minimizes or eliminates the need to use preservatives or bacteriostatic compounds in the substances administered, without risking contamination. In addition, if the unit dosage form is damaged, or is otherwise defective, the devices do not administer the substance, which may no longer be sterile. For example, if an unit dosage form is defective in the area of the pierceable section, or develops a leak, the devices will not dispense the substance properly because sufficient pressure will not be generated in the unit dosage form to effectively release the substance.

The dosage forms of the disclosure are described, in certain embodiments as including a dispensing blister chamber that contain a piercing device, wherein the piercing device is a substantially hollow, elongate member with a base end and a piercing tip opposite the base end and providing a discharge nozzle. In certain embodiments the dispensing blister conforms to at least the base end of the piercing device effective to support and hold the piercing device in place during manufacture and use of the dosage form. The piercing devices include one or more inlet openings on or near the base end and an internal conduit providing fluid communication between the one or more inlet ports and the discharge nozzle; and the surface of the internal conduit comprises structural features such as contours, steps, flutes, ribs, constrictions, or a combination thereof to control the spray pattern and droplet size of a fluid forced through the piercing device. It is a further aspect of the disclosure that the inlet openings provide a fluid path from the interior of the dispensing blister chamber into the internal conduit that comprises one or more bends, and that the combination of angular turns and the structural features of the internal conduit create vortices in the fluid as it is forced through the piercing mechanism.

The structural features can be designed, for example, for different types of spiral, vertical and other flow and the design can be adjusted for different viscosities of the fluid or solid to be dispensed. For example, structural features may be added to create a vortex, to further mix the contents of the blister, to change the fluid property type from laminar to turbulent or vice versa or to change fluid properties such as pressure, velocity, surface tension or viscosity and can also aid in reconstitution of lyophilized or powdered agents. Additionally, the inlets into the internal conduit can include bends of angles from about 1° to 90°, or more in combinations in order to create the desired spray plume geometry for a particular medicament or liquid dose.

In certain embodiments, a shaped blister dosage form as described herein that contains medication and an internal piercing nozzle, is configured for use in a smaller diameter dispensing mechanism, while still providing an accurate dose of medicine in the form of a controlled spray. A blister strip including a plurality of such dosage forms can include a blister material layer in which the dosage forms are formed, and a lid material bonded to the blister material. A concentric sealing area provides a resilient seal that is not broken when the dosage forms are crushed to deliver the contained medication.

To produce a controlled spray of liquid when bursting a sealed formed recess, such as a shaped blister, an internal piercer inside the sealed blister may be used, and may be positioned such that it maintains contact with the lid material. The internal piercer can be constructed of any suitable materials such as ceramic, glass, metal, styrene, polystyrene, plastics, including but not limited to PET, polypropylene, polyethylene, or PEEK, and other pharmaceutical grade FDA approved materials of sufficient hardness to penetrate the lid material. The second, subsequent and/or final plunger(s) may be designed to shape the formed recess such that the internal piercer is locked into place within the formed recess, e.g., through manufacture, handling, transportation, storage, and actual use. For example, in a shaped blister, a protruding structure, an indentation, a diaphragm or an annulus is formed to conform to the shape of the base of the internal piercer. The protruding structure, indentation, diaphragm, or annulus provides support for and holds the internal piercer in place during assembly and during dispensing. Thus, these structures function to capture the internal piercer (e.g., restrict vertical movement of the piercer), thereby holding it in place. The internal piercer may also be held in place through manufacture and actual use by, for example, press fit, welding, hydrostatic forces, or electrostatic forces. The shaped blister can also be formed by the second or subsequent plunger such that it insures that the protruding structure, indentation, diaphragm, or annulus seals to the internal piercer in order to achieve the desired spray pattern.

In preferred embodiments, the internal piercer includes a hollow tube or channel (the delivery channel) through which the pharmaceutical dosage flows as the shaped recess is compressed and pierced. The tip of the piercer can be in the shape of a nipple, or a projection from the main body in order to reduce the formation of a puncture flap in the lid material after puncture. The inside diameter of the piercer tube can range from about 0.010 inches to about 0.05 inches, but in certain preferred embodiments is about 0.025 inches. The internal diameter, shape, or surface texture of the delivery channel, whether in, near, and/or at the exit point, may contain a nozzle or may be varied to form the optimum droplet size and spray plume geometry of the pharmaceutical dosage form as it exits the shaped article, as well as control the velocity, pressure, pattern, distribution, and aim of the released substance. Thus, the nozzle system and the piercer may be integrated into a single unit. The nozzle system can also be designed to determine the mixing of the substance as it is released.

To successfully dispense the medication, the medication must flow through the piercing nozzle with the correct magnitude and vectors of velocity to create the desired spray geometry. As described herein, this is accomplished by pressing on the blister form with sufficient force to push the piercing nozzle through the lid material, completely crushing the dosage form and forcing the contents through the nozzle with the required velocity. During this dispensing operation, the seal of the lid material to the blister material must be strong enough that no leakage occurs prior to the nozzle piercing the lid. The smaller size required by certain dosage situations, such as intranasal administration present greater challenges to the seal of the lid material to the blister material.

In certain embodiments the piercing mechanism is contained in the dosage form with the fluid to be delivered. Such internal piercing mechanisms can include an internal chamber, one or more inlet openings arranged to force one or more bends or changes in direction as the fluid flows into the internal chamber, a discharge outlet, and features on the internal surface to control the spray pattern and droplet size of a fluid forced to flow through the nozzle. The changes in direction can be of any appropriate angle, including from about 1° to about 90° or more. The design of such features are known to those of skill and include steps, flutes, ribs, or a combination thereof.

In certain embodiments the disclosure may be described as a piercing nozzle for dispensing fluid from a dosage form in a controlled spray pattern and droplet size. The nozzle includes a substantially elongate oval shaped member with an inlet end and a nipple shaped discharge end, an internal channel connecting the inlet end and the discharge end in fluid communication, one or more inlet openings in the inlet end, a discharge opening in the discharge end, and features on the internal chamber surface to control the spray pattern and droplet size of a fluid forced through the nozzle. The inlet ports are designed to provide a fluid path into the internal channel that includes one or more right angle turns. The inlet ports can also be designed to produce a vortex in the liquid as it is forced through the ports. Features in the internal channel can also include, but are not limited to steps, flutes, ribs, and related structures to produce the desired droplet size and spray geometry. In certain embodiments, the piercing tip may be on the discharge end of the elongated member, or on the inlet end. The piercing nozzle can be contained in a dosage form. The disclosure includes, therefore, a dosage form containing the piercing nozzle and a medical or pharmaceutical composition.

In certain embodiments the present disclosure can be described as an internally pierced dosage form that includes a substantially dome shaped, flexible blister, a substantially round pierceable surface sealed to the base of the dome-shaped blister, and an internal chamber containing a piercing nozzle as described herein and a liquid composition. In certain embodiments the piercing nozzle includes a base and a piercing end, and wherein the base is attached to the dome shaped blister and the piercing end is proximate the piercable surface.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1:
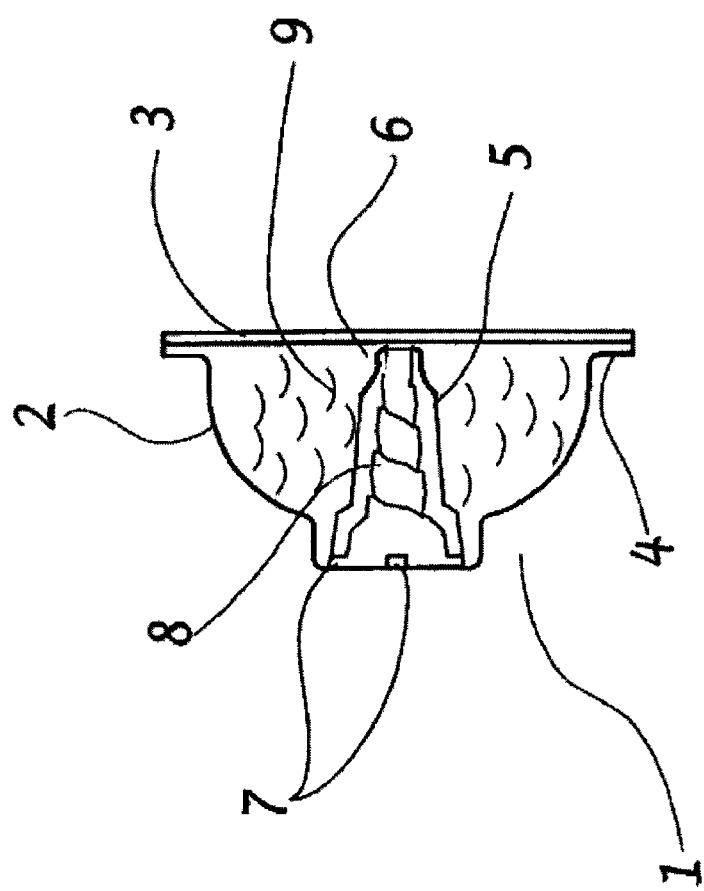
FIG. 1 is an embodiment of a dosage form with an internal piercing mechanism.

Preferred embodiments of the present disclosure are directed to dosage forms that contain a measured dose of one or more pharmaceutically active agents and a piercable section such that the dosage form can be pierced to release the contents under pressure. When using the term "under pressure" in the disclosure, it is understood that the pressure is typically an externally applied pressure rather than internal pressure within the dosage form itself. In typical operation, a plunger, lever, ram, wheel, or some other mechanical device contacts the dosage form with sufficient force to crush the dosage form against a piercing member and force the contents out of the opening. The dosage form can be generated using methods well known to those of skill in the art, including, for example, form fill seal technology or blow fill seal technology, or by deep draw forming as described in U.S. Application Publication No. 2009/0071108, incorporated herein in its entirety.

The form-fill-seal process can be used to create a blister, for example a blister pack, from rolls of flat sheet or film, inserted with a piercing mechanism, filled with the pharmaceutically active agent, and closed or sealed on the same equipment. This process involves a formed base which has the cavity in which the pharmaceutically active agent, or an agent that may be mixed or combined with a pharmaceutically active agent, is placed, and a lidding, for example of foil, through which the agent is dispensed out of the blister. Blow fill seal technology involves forming, filling, and sealing a dosage form in a continuous process in a sterile enclosed area inside a machine.

The film layer may include a variety of different materials, including, but not limited to, thermoplastics, polymers, copolymers, composites and laminates. When the unit dose is a pharmaceutical dosage form, the film will need to be able to undergo aseptic manufacturing processes to produce sterile shaped articles, for example gamma ray irradiation. Preferably the film is flexible but capable of holding its shape, can be crushed with minimal force, creates a barrier, withstands radiation, and has desirable chemical properties (e.g., does not react with the pharmaceutical dosage form to be administered). For blister packs, the film is preferably a foil laminate, and more preferably a metal-plastic laminate. The metal-plastic laminate comprises a metal foil coated on at least one side, or on both sides, with a plastic layer. If the metal-plastic laminate comprises a plastic layer on both sides of the metal foil, the plastic layers may be the same type of plastic layer, or different types of plastic layers.

Materials which may be used in the plastic layer of the laminate are well known by those skilled in the art and include, but are not limited to, a variety of commercially available polymers and copolymers, such as polyvinylchloride, nylon, nylon derivatives, polybutylene terephthalate, polyethylene terephthalate, polyethylene, polypropylene, polystyrene, polyacetal, vinylidene chloride, propylene ethylene copolymers, polyethylene napthalate, fluoropolymers, cyclic polyolefins, polyamides, and similar materials or combinations thereof. The plastic layer may be present in the laminate at a thickness of about 8 μm to about 80 μm, about 10 μm to about 70 μm, about 15 μm to about 60 μm, about 20 μm to about 50 μm, or about 25 μm to about 40 μm, and any ranges therein. The plastic components may be non-stretched, or alternatively uniaxially or biaxially stretched, or may be thermoplastics such as halogen-containing polymers, polyolefins, polyamides, polyesters, acrylnitrile copolymers, or polyvinylchlorides. Typical examples of thermoplastics of the polyolefin type are polyethylenes such as low density polyethylene (LDPE), medium density polyethylene (MDPE), high density polyethylene (HDPE), uniaxially, or biaxially stretched polypropylenes, polypropylenes such as cast polypropylene and uniaxially or biaxially stretched polyethylene terephthalate (PET) from the polyester series. The above examples are in no way meant to be limiting, as other materials known in the art may be used in the plastic layer as well.

Examples of plastics based on halogen-containing polymers include but are not limited to polymers of vinylchloride (PVC) and vinyl plastics, containing vinylchloride units in their structure, such as copolymers of vinylchloride and vinylesters of aliphatic acids, copolymers of vinylchloride and esters of acrylic or methacrylic acids or acrylnitrile, copolymers of diene compounds and unsaturated dicarboxyl acids or their anhydrides, copolymers of vinylchloride and vinylchloride with unsaturated aldehydes, ketones, etc., or polymers and copolymers of vinylidenchloride with vinylchloride or other polymerizable compounds. The vinyl-based thermoplastics may also be made soft or pliable in a conventional manner by means of primary or secondary softeners.

If the plastic films comprise polyesters (PET-films), examples of polyesters include but are not limited to polyalkylene-terephthalate or polyalkylene-isophthalate with alkylene groups or radicals with 2 to 10 carbon atoms or alkylene groups with 2 to 10 carbon atoms interrupted by at least one oxygen atom, such as, e.g., polyethylene-terephthalate, polypropylene-terephthalate, polybutylene-terephthalate (polytetramethylene-terephthalate), polydecamethylene-terephthalate, poly 1,4-cyclohexyldimethylol-terephthalate or polyethylene-2,6-naphthalene-dicarboxylate or mixed polymers of polyalkylene-terephthalate and polyalkylene-isophthalate, where the fraction of isophthalate amount, e.g., to 1 to 10 mol. %, mixed polymers and terpolymers, also block polymers and grafted modifications of the above mentioned materials. Other useful polyesters are known in the field by the abbreviation PEN. Other polyesters are copolymers of terephthalic acid, a polycarboxyl acid with at least one glycol, copolymers of terephthalic acid, ethyleneglycol and an additional glycol, polyalkylene-terephthalates with alkylene groups or radicals with 2 to 10 carbon atoms, polyalkylene-terephthalates with alkylene groups or radicals with 2 to 10 carbon atoms which are interrupted by one or two oxygen atoms, polyalkylene-terephthalates with alkylene groups or radicals with 2 to 4 carbon atoms, and polyethyleneterephthalates (e.g., A-PET, PETP, PETG, G-PET). Glycol-modified polyesters are also referred to as PETG.

Examples of polyolefins for plastic films include but are not limited to polyethylenes (PE), e.g., high density polyethylene (HDPE, density larger than 0.944 g/cm), medium density polyethylene (MDPE, density 0.926-0.940 g/cm), linear polyethylene of medium density (LMDPE, density 0.926.0.940 g/cm), low density polyethylene (LDPE, density 0.910-0.925 g/cm), and linear low density polyethylene (LLDPE, density 0.916-0.925 g/cm), for example as non oriented (PE film) or uniaxially or biaxially oriented films (oPE film), polypropylenes (PP), such as axially or biaxially oriented polypropylene (oPP film), or cast polypropylene (cPP film), amorphous or crystalline polypropylene or mixtures thereof, ataktic or isotaktic polypropylene or mixtures thereof, poly-1-butene, poly-3-methylbutene, poly-4-methylpententene and copolymers thereof, polyethylene with vinylacetate, vinylalcohol, acrylic acid, such as, e.g., ionomeric resins, such as copolymers of ethylene with 11% acrylic acid, methacrylic acid, acrylic esters, tetrafluorethylene or polypropylene, statistical copolymers, block polymers or olefin polymer-elastomer mixtures, ionomers, and ethylene-acrylic acid copolymers (EAA).

If the plastic films comprise polyamide films (PA), examples of polyamides include but are not limited to polyamide 6, a homo-polymer of [ε]-caprolactam (polycaprolactam); polyamide 11, polyamide 12, a homo-polymer of [ω]-laurinlactam (polylaurinlactam); polyamide 6,6, a homo-polycondensate of hexamethylenediamine and adipinic acid (polyhexa-methylene-adi-amide); polyamide 6,10, a homo-polycondensate of hexa-methylene-diamine and sebacinic acid (poly-hexa-methylene-sebacamide); polyamide 6,12, a homo-polycondensate of hexa-methylene-diamine and dodecandic acid (poly-hexa-methylene-dodecanamide) or polyamide 6-3-T, a homo-polycondensate of trimethyl-hexa-methylene-diamine and terephthalic acid (poly-trimethyl-hexa-methylene-terephthalic-amide), and mixtures thereof.

If the plastic comprise acrylnitrile-copolymers, examples of acrylnitrile-copolymers include but are not limited to copolymers of acrylnitrile or methacrylnitrile with acrylic acid esters, vinyl-carboxylate esters, vinyl halides, aromatic vinyl compounds or unsaturated carboxylic acid and diene, and acrylnitrile-methylacrylate copolymers.

Metals which may be useful in the foil component of the laminate are those that can be formed into a foil with the physical and chemical properties (e.g., thickness, malleability, temperature resistance and chemical compatibility) sufficient to adhere to the plastic layer(s) and remain intact during the forming processes disclosed herein. Such metals include, but are not limited to, aluminum, iron, nickel, tin, bronze, brass, gold, silver, chrome, zinc, titanium, and copper, combinations thereof, as well as alloys including the aforementioned metals, such as steel and stainless steel. The metal foil may be present in the laminate, for example, at a thickness of about 8 μm to about 200 μm, about 10 μm to about 150 μm, about 15 μM to about 125 μm, about 20 μm to about 100 μm, or about 25 μm to about 80 μM, and any ranges therein. In certain embodiments the foils, e.g., aluminum foil, may have a purity of at least about 98.0%, more preferably at least about 98.3%, still more preferably at least about 98.5%, and most particularly at least about 98.6%. Aluminum foils of the aluminum-iron-silicon or aluminum-iron-silicon-manganese types may also be used. Other suitable metal foils known in the art may be used as well.

The laminate may also include one or more adhesive layers between the foil layer and the plastic layer. The same or different adhesives may be used to adhere the plastic to the metal foil on each side. The adhesive layer should be capable of forming a bond with the plastic layer and the foil layer, and generally should be of a thickness of between about 0.1 μm and about 12 μm, more typically between about 2 μm and about 8 μm, and any ranges therein. Any number of adhesives known in the art may be used, and the adhesives may be applied using a number of known techniques. Suitable adhesives may contain one or more solvents, be solvent-free, or may be acrylic adhesives or polyurethane adhesives. The adhesive may also be a thermal bonding adhesive, for example an ethylene-vinylacetate copolymer or a polyester resin. The adhesive may also be of a type which hardens upon exposure to electromagnetic rays, for example ultraviolet rays. The laminate may also be formed by hot calendaring, extrusion coating, co-extrusion coating or through a combination of processes. Example adhesives that may be used in the present disclosure include but are not limited to polyethylene (PE) homopolymers, such as LDPE, MDPE, LLDPE, and HDPE; PE copolymers, such as ethylene-acrylic acid copolymers (EAA), ethylene methacrylic acid copolymer (EMAA); polypropylene (PP); PP copolymers; ionomers; and maleic anhydride grafted polymers.

In another embodiment, the film, e.g., a metal-plastic laminate, may feature a sealing layer in the form of a sealable film or a sealable counting on one of the outer lying sides, or on both of the outer sides. The sealing layer will be the outermost layer in the laminate. In particular, the sealing layer may be on one outer side of the film, which is directed towards the contents of the shaped packaging, in order to enable the lid foil or the like to be sealed into place.

Another embodiment for forming blister packaging is a laminate of aluminum, where the metal foil is coated with a plastic on each side. Aluminum foil is known to provide superior barrier properties to protect the contents of the package. The plastic coating provides an effective means of sealing the package plus provides a protective coating for the aluminum, and may also provide the ability to print on the package.

In some embodiments, the thicknesses and compositions of the laminate include but are not limited to:
  i. OPA/ALU/PE (12 μm/60 μm/30 g/m$^2$);
  ii. OPA/ALU/PE (12 μm/45 μm/30 g/m$^2$);
  iii. OPA/ALU/PVC (12 μm/60 μm/30 g/m$^2$);
  iv. OPA/ALU/PVC (12 μm/45 μm/30 g/m$^2$);
  v. OPA/ALU/PP (12 μm/60 μm/30 g/m$^2$); and
  vi. OPA/ALU/PP (12 μm/45 μm/30 g/m$^2$). As used above, OPA stands for oriented polyamide, ALU stands for aluminum, PE stands for polyethylene, PVC stands for polyvinylchloride, and PP stands for polypropylene.

An example of a dosage form with an internal piercing member is shown in FIG. 1. The dosage form in FIG. 1 is a blister dosage form 1 that includes a diaphragm 2 formed into a dome shape and a membrane 3 sealed to the diaphragm 2 along the seal area 4. Sealed within the blister dosage form 1 are a piercing nozzle 5 and a liquid composition 9.

Figure 2:
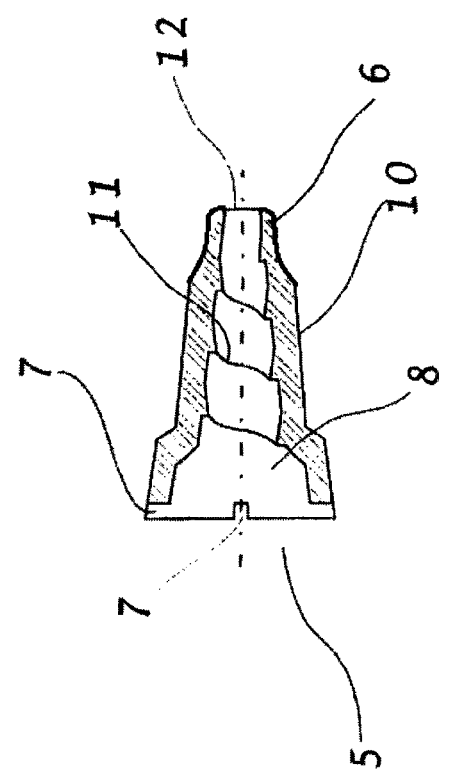
FIG. 2 is an embodiment of a piercing mechanism.

The piercing nozzle of FIG. 1 is also shown in FIG. 2. This example of a piercing nozzle 5 has tapered sides 10 and an inner chamber 8 that connects inlet ports 7 to a discharge port 12. The inner chamber 8 can contain internal contours 11 and other structures on the interior walls of the inner chamber 8. The contours and other structures are designed to influence the flow of the fluid or solid agent 9. Different nozzle configurations are created for specific applications to cause the fluid or solid agent to exit the discharge port 12 in a spray, mist or stream, depending on the needs of a specific medication or application.

Figure 3:
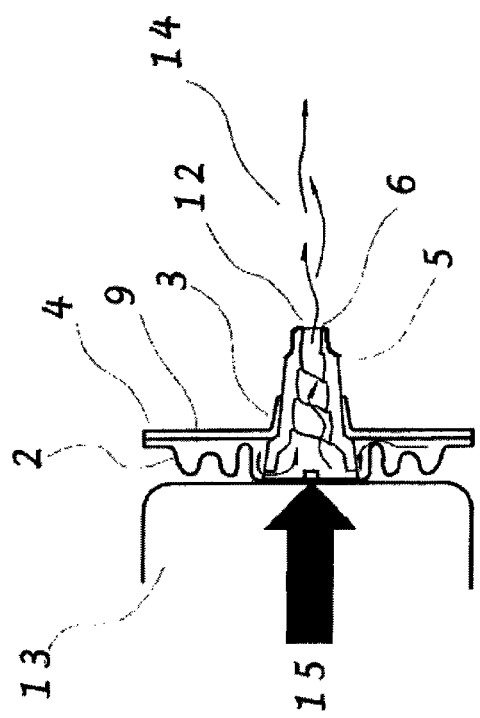
FIG. 3 demonstrates an embodiment of a dosage form with an internal piercing mechanism during administration of the contents.

A blister dosage form is shown during use in FIG. 3. When the dose is to be administered, the dosage form is placed in a device designed to administer the pharmaceutical agent to a particular location, such as in the eye, ear, nose, mouth, lungs or skin of a user, for example. The device may administer the pharmaceutical agent through oral, peroral, enteral, parenteral, pulmonary, rectal, otic, topical, nasal, vaginal, lingual, direct injection, intravenous, intraarterial, intracardial, intradermal, intramuscular, intraperitoneal, intracutaneous, intraocular, ophthalmic, intranasal, intrapleural, intrathecal, intratumor, intrauterine, orthotopic, transdermal, buccal, and subcutaneous or other routes of delivery. Many such devices include a firing mechanism that drives a ram against the dosage form with an explosive force. Examples of such devices are described in pending U.S. Application Publication No. 2008/0177246, incorporated herein in its entirety by reference. The results of this action are demonstrated in FIG. 3, in which a force in the direction 15 is applied with a plunger 13 to the back of the domed diaphragm 2. The piercing tip 6 has penetrated the membrane 3 and the liquid medication 9 has flowed into the inner chamber 8 through the inlet ports 7, out the discharge port 12 and been dispensed in a discharge pattern 14. The piercing tip 6 and tapered sides 10 of the piercing nozzle 5 cause the membrane 3 to seal tightly around the piercing nozzle 5 forcing the medication 9 to flow out the discharge port 12.

Figure 4:
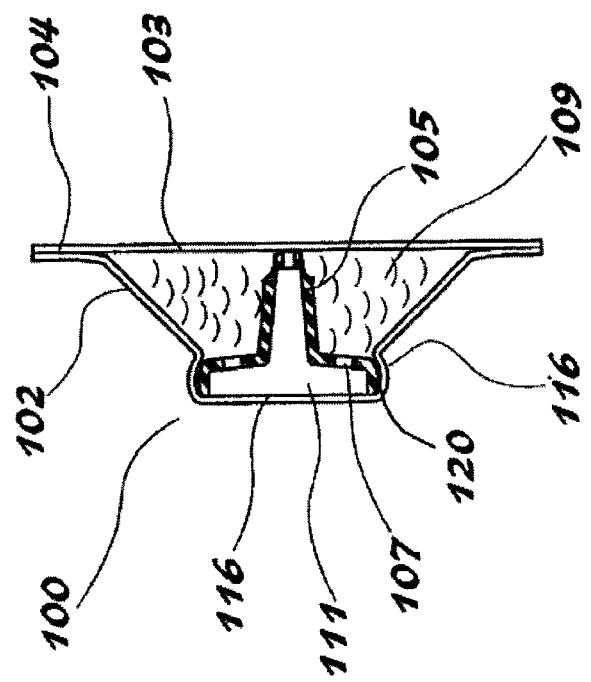
FIG. 4 is an embodiment of a dosage form with an internal piercing mechanism.

Another embodiment of a blister dosage form 100 is shown in FIG. 4. This version has the inlet ports 107 on the same side of the piercing nozzle 105 as the discharge port 112. This configuration forces the components 109 to flow through two 90° bends during dispensing. It is understood that the bends or turns in the delivery channel, or even in the entry ports are not constrained to 90°, but can be designed for particular applications as one or more bends or turns of from 45° to 135° inclusive, or to any angle within that range in discrete bends connected by straight channels, or in a serpentine form to create the desired amount of turbulence in the delivered dose. Forcing the liquid or solid agent to flow through this series of bends or turns in conjunction with the contours 111 in the inner chamber 108 control the discharge pattern 114. In blister dosage form 100 a portion 116 of diaphragm 102 is formed to conform to the shape of the base 120 of the piercing nozzle. The diaphragm provides support for and holds the piercing nozzle 105 in place during assembly and during dispensing. Thus, the diaphragm functions to capture the piercing nozzle and hold it in place through manufacture and actual use.

Figure 5:
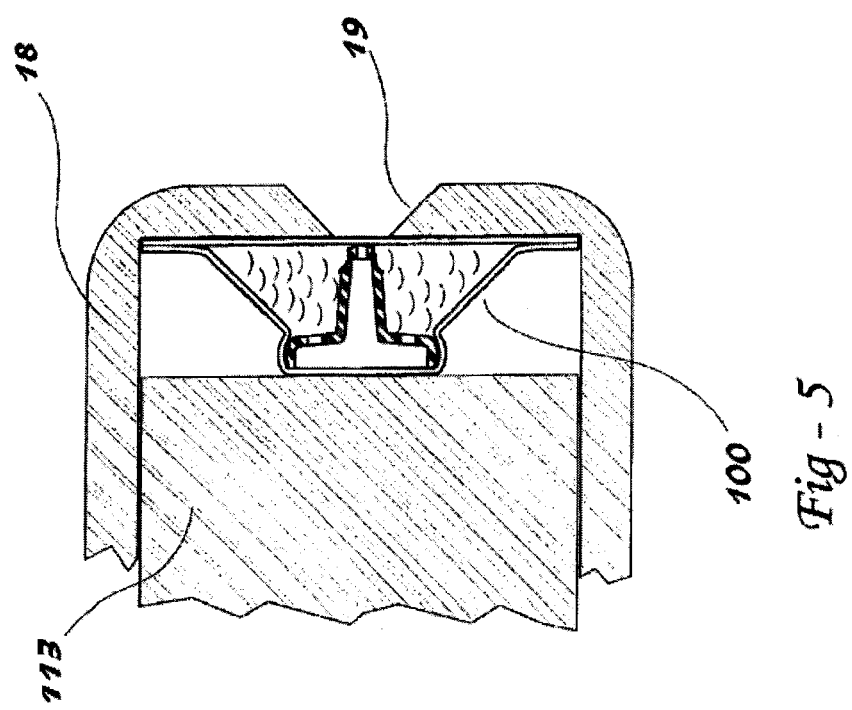
FIG. 5 is a view of the embodiment of FIG. 4 in the housing of a device for administering the dosage.
Figure 6:
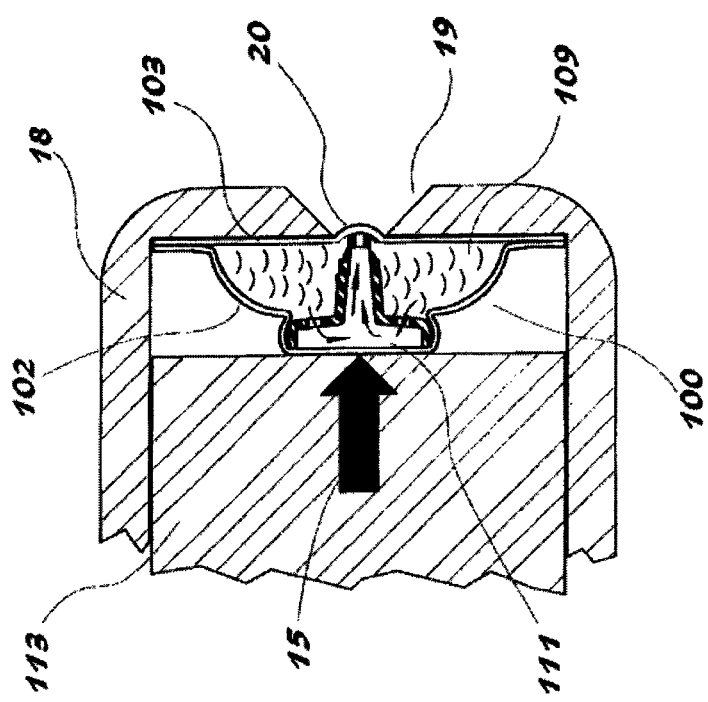
FIG. 6 is a view of the dosage form of FIG. 5 during an intermediate step of administration.
Figure 7:
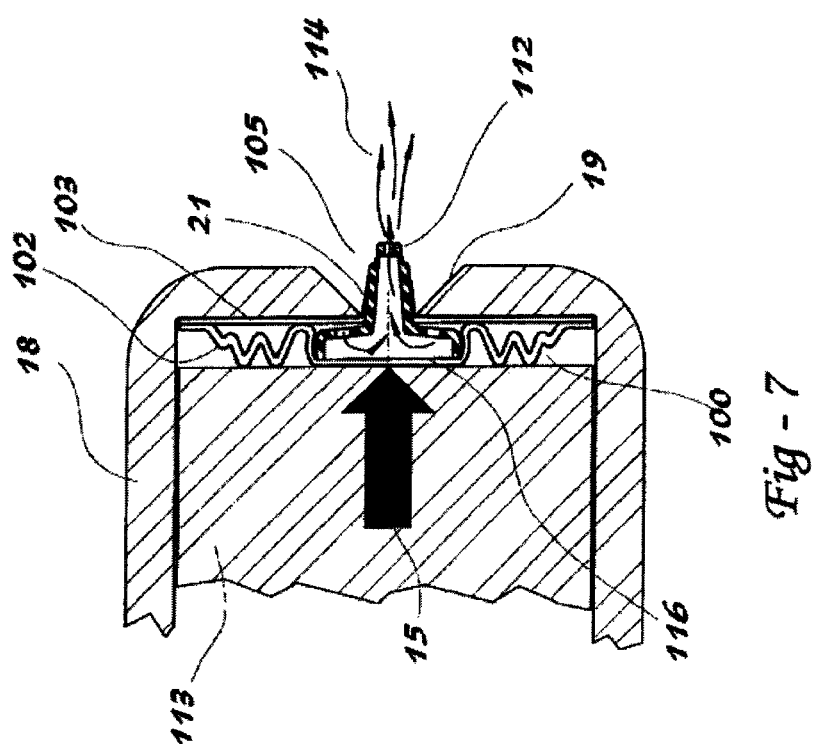
FIG. 7 is a view of the dosage form of FIG. 5 during discharge.

Blister dosage form 100 is shown in FIG. 5 positioned in a housing 18 with plunger 13 in the ready mode. Housing 18 has a discharge opening 19 to allow the piercing nozzle 105 to penetrate the membrane 103 during dispensing. The membrane 103 is sealed to diaphragm 102 at seal area 104. As shown in FIG. 6, a force in direction 15 is applied to plunger 13 during the dispensing action, compressing the diaphragm 102 and driving the piercing nozzle 105 into the membrane 103 at piercing point 20. The next stage of dispensing is shown in FIG. 7. As the force continues to drive the plunger 113 against the diaphragm 102, the diaphragm collapses, driving piercing nozzle 105 through the membrane and forcing the agent 109 through the piercing nozzle 105 and out the discharge port 112 in the discharge pattern 114. In this embodiment, the shape of the blister dosage form 100 is designed to conform to the plunger 113 and housing 18 of the dosing mechanism to insure that the diaphragm 102 seals to the piercing nozzle 105 in the contact area 116 and that the membrane 103 is stretched away from the fissure point to minimize flap formation and interference in sealing area 21 in order to achieve the desired spray pattern 114.

Figure 8:
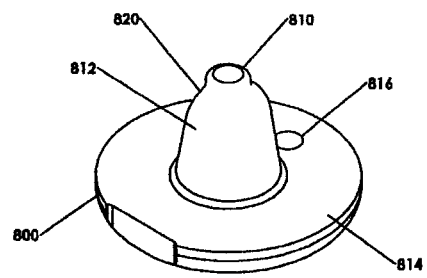
FIG. 8 is a perspective view of a piercing device.

An embodiment of a piercing device 800 is shown in FIG. 8 in which the piercing tip 810 is formed as a projection or nipple concentric with the delivery opening 818 in the elongated, oval shaped body 812 of the piercer. Also shown in this view is the base 814 and the entry port 816. The nipple is designed and sized to be the first contact point with the film and to stretch the film to create a non-contact region between the initial contact point and the shoulder region 820 or edge of the body. This interaction is shown in more detail in FIG. 12.

Figure 9:
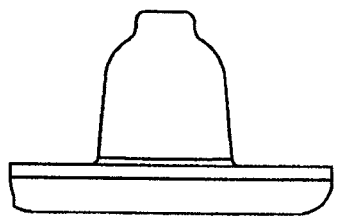
FIG. 9 is a side view of the piercing device as in FIG. 8 showing the long axis of the oval shaped piercer.
Figure 10:
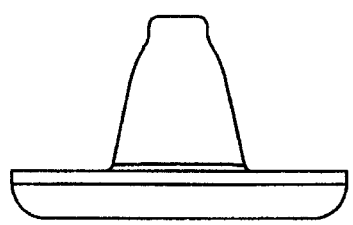
FIG. 10 is a side view of the piercing device as in FIG. 2 rotated 90° to show the short axis of the oval shaped piercer.

FIG. 9 is a side view of the piercing device as in FIG. 8 showing the long axis of the oval shaped body and can be compared to FIG. 10, which is rotated 90° from the perspective in FIG. 9, to show the short axis of the oval shaped body.

Figure 11:
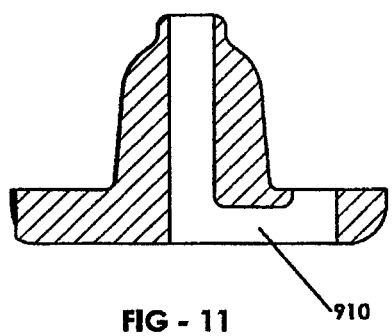
FIG. 11 is a cross sectional view of a piercer as in FIG. 8 showing the fluid path.

FIG. 11 is a cross sectional view of a piercer as in FIG. 8 showing an example of a fluid path 910 through the base 814 of the piercing device. It is understood that although a single entry port is shown, a device can include one or more entry ports spaced around the base of the device.

Figure 12:
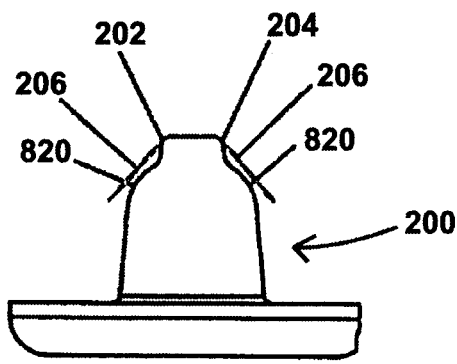
FIG. 12 is a view of an oval shaped piercer with a nipple shaped tip at the point of first fissure in piercing a film stock.

FIG. 12 is a magnified view of an oval shaped piercer body 200 with a nipple shaped tip 202 at the point of first fissure in piercing a film 204. As shown in the drawing, the film 204 is stretched by the tip 202 prior to the initial fissure or opening in the film. As the film is stretched a drape is formed that includes a non-contact region 206 stretched between the tip 202 and the shoulder region 820 of the piercer body 200. As used herein, the drape is that portion of the film that is in direct interaction with the piercing tip. The contact part of the drape is that portion that directly contacts the piercer tip or body and the non-contact drape is that portion that does not directly contact the piercer. The novel shape of the piercer shown in FIG. 12 is found to form a large non-contact drape area that is between the tip and the shoulder region of the long axis sides of the oval shaped piercer body that pull the film away from the center axis of the piercer. The shorter or minor axis sides of the piercer can also create a non-contact drape region if the outer edge is substantially extended outwardly relative to the circumference of the nipple or tip region. The oval shape of the preferred embodiment is, therefore, not a critical shape but does lend itself to efficient manufacturing of the devices. Other cross sectional shapes at the shoulder region, therefore, such as circular, rectangular or other angular shapes, or shapes with projections or fingers would also be effective to create non-contact drape areas and are contemplated to be effective at preventing or inhibiting interference with the spray pattern by a flap during use.

Figure 13:
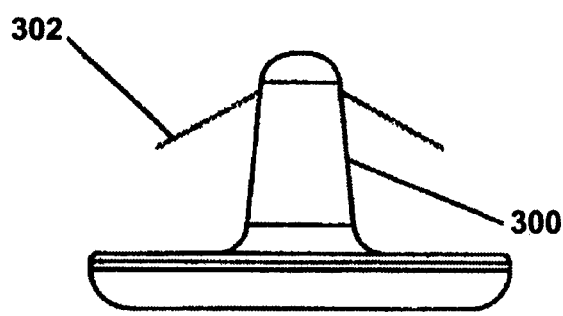
FIG. 13 is a view of a prior art piercer at the point of first fissure in piercing a film stock.

FIG. 13 is a view of a rounded tip piercer at the point of first fissure in piercing a film. The piercer body 300 has a circular cross section and there is no nipple region, and therefore no shoulder region is created. As can be seen in this drawing, little or no non-contact drape is formed by the film 302 at first fissure. Since the film is not being biased away from the center of the piercer, a relatively large flap is created over the center of the piercer that can interfere with the spray during use.

Figure 14:
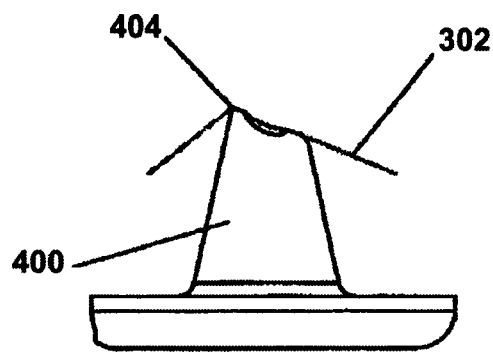
FIG. 14 is a view of a sharp tipped piercer at the point of first fissure in piercing a film stock.

FIG. 14 is a view of a piercer 400 with a sharp tipped piercing point 404, which is the point at which the first fissure in film 302 is formed. Because the film is stretched and penetrated at a single point, little to no non-contact drape is formed, and an interfering flap is present during use.

Example

A study was undertaken to demonstrate and to explain the surprisingly superior performance of an oval shaped piercer with a nipple tip over other configurations in reducing the formation of puncture flaps in internally pierced blister dosage forms. It has been discovered by the present inventor that the cause of puncture flaps is the dynamic between the location of the first fissure in the film or lidstock and the nature of the piercer body/lidstock contact.

As shown herein, a piercer configuration that creates a substantial non-contact drape between the tip and piercer body provides a significant improvement in delivery efficiency by reducing or inhibiting puncture flap formation.

As illustrated in FIGS. 12-14, the first fissure occurs at the distal end of the piercer where the tip first contacts the lidstock. This occurs on one edge of the tip. If there is significant lidstock-piercer contact on the other side of the tip, that material forms a flap. The greater the contact area on the tip of the piercer, the larger the flap. Conversely, as the non-contact drape increases the size of the flap is reduced.

Without limiting the disclosure to any particular theory, it is contemplated that the non-contract drape is under tension as the first fissure occurs and this tensioned film acts as a spring when the fissure occurs, snapping the extra material down and away from the delivery channel. If there in little or no non-contact drape then this spring action does not occur.

If, for example, one side of the fissure is strongly non-contacting and the other side is minimally contacting, then the flap interference is minimized. If one side of the fissure is strongly non-contacting and the other side is strongly contacting, the flap interference is increased.

It is an aspect of the disclosed piercer design, therefore, that the non-contacting drape is maximized and the contact area is minimized. This maximizes the spring action and minimizes the flap interference with dose delivery.

An example of increased efficiency obtained by the novel design is shown below.

TABLE 1

|  | Ovalized with nipple Piercer | Round Piercer |
| --- | --- | --- |
| Delivered vol. (µl) | 26 of 34 | 29 of 48 |
| Errant vol. (µl) | <2 | 12 |
| Residual vol. (µl) | <6 | 7 |
| Delivery efficiency | ≥76.5% | 60% |

All of the devices and methods disclosed and claimed herein can be made and executed without undue experimentation in light of the present disclosure. While the devices and methods of this invention have been described in terms of preferred embodiments, it will be apparent to those of skill in the art that variations may be applied to the devices and/or methods and in the steps or in the sequence of steps of the methods described herein without departing from the concept, spirit and scope of the invention. All such similar substitutes and modifications apparent to those skilled in the art are deemed to be within the spirit, scope and concept of the invention as defined by the appended claims.

The invention claimed is:

1. A piercing device for delivering a predetermined quantity of medicament contained in a crushable blister into a spray or mist, said device comprising:
a base; a
substantially hollow, elongated member extending from the base comprising a main body region and terminating in a piercing tip region and wherein the circumference of the tip region is substantially smaller than the circumference main body region and a shoulder region that separates the main body region from the tip region;
an internal delivery channel formed by the hollow interior of the elongated member extending from the base to the tip and terminating in a discharge port at the piercing tip;
one or more inlet ports in the base and one or more conduits providing fluid communication between the one or more inlet ports and the internal channel;
wherein the difference in circumference of the tip region and the main body region is effective to form a non-contact drape region on opposites sides of the tip when the tip is pressed into a flexible material.

2. The piercing device of claim 1, further comprising structural features on the surface of the internal delivery channel to affect the spray pattern and droplet size of a fluid forced through the piercing device during use.

3. The piercing device of claim 2, wherein the features on the internal surface of the internal delivery channel comprise steps, flutes, ribs, or a combination thereof.

4. The piercing device of claim 1, wherein at least one of the conduits from an inlet port to the internal channel comprises one or more bends or turns.

5. The piercing device of claim 4, wherein one or more of the bends or turns is an angle of from 45° to 135°.

6. The piercing device of claim 1, wherein at least one of the conduits from an inlet port to the internal channel comprises one or more 90° turns.

7. The piercing nozzle as described in claim 1, wherein the one or more inlet ports are arranged to produce a vortex in fluid forced through the delivery channel during use.

8. The piercing device of claim 1, where the elongated member has an elliptical cross-section; wherein the projected piercing tip is concentric with the elliptical member, the major axis of the ellipse is from about 1 to 1.5 times the minor axis and the diameter of the projected tip is less than 50% of the major axis of the ellipse where the tip projects from the shoulder region.

9. A dosage form containing the piercing device of claim 1 and a medical composition.

10. An internally pierced dosage form comprising:
a flexible blister with a circular base defining an internal chamber;
a planar sheet of piercable material sealed to the base of the blister;
and a piercing device and a medical composition contained in the internal chamber;
and wherein the piercing device comprises:
a base;
a substantially hollow, elongated member extending from the base comprising a main body region and terminating in a piercing tip region and wherein the circumference of the tip region is substantially smaller than the circumference of the main body region and a shoulder region separating the main body region from the tip region;
an internal delivery channel formed by the hollow interior of the elongated member extending from the base to the tip and terminating in a discharge port at the piercing tip; and
one or more inlet ports in the base and one or more conduits providing fluid communication between the one or more inlet ports and the internal channel;
wherein the difference in circumference of the tip region and the main body region is effective to form a non-contact drape region of a flexible material between the tip and the shoulder region on opposites sides of the tip when the tip is pressed into the flexible material.

11. The dosage form of claim 10, wherein the piercing device further comprises structural features on the surface of the internal delivery channel to affect the spray pattern and droplet size of a fluid forced through the piercing device during use.

12. The dosage form of claim 11, wherein the features on the internal surface of the internal delivery channel comprise steps, flutes, ribs, or a combination thereof.

13. The dosage form of claim 11, wherein at least one of the conduits from an inlet port to the internal channel comprises one or more bends or turns.

14. The dosage form of claim 12, wherein one or more of the bends or turns is an angle of from 45° to 135°.

15. The dosage form of claim 10, wherein at least one of the conduits from an inlet port to the internal channel comprises one or more 90° turns.

16. The dosage form of claim 10, wherein the one or more inlet ports are arranged to produce a vortex in the fluid as it is forced through the delivery channel.

17. The dosage form of claim 10, where the elongated member has an elliptical cross-section; wherein the projected piercing tip is concentric with the elliptical member, the major axis of the ellipse is from about 1 to 1.5 times the minor axis and the diameter of the projected tip is less than 50% of the major axis of the ellipse where the tip projects from the shoulder region.

18. The dosage form of claim 10, wherein the base of the piercing device is attached to the blister opposite the piercable material and the piercing tip is proximate the piercable material.

19. A piercing device for delivering a predetermined quantity of medicament contained in a crushable blister in a spray or mist, said device comprising:
a base;
a substantially hollow elongated member extending from the base and comprising a main body with an oval shaped cross-section, a piercing tip region and a shoulder region between the main body and the piercing tip region; and
wherein the circumference of the tip region is substantially smaller than the circumference main body region;
an internal delivery channel formed by the hollow interior of the elongated member extending from the base to the tip and terminating in a discharge port at the piercing tip; and
one or more inlet ports in the base and one or more conduits providing fluid communication between the one or more inlet ports and the internal channel;
wherein the difference in circumference of the tip region and the main body region is effective to form a non-contact drape region between the tip and the shoulder region on opposites sides of the tip when the tip is pressed into a flexible material.

20. A piercing device for delivering a predetermined quantity of medicament contained in a crushable blister into a spray or mist, said device comprising:
a base;
a substantially hollow, elongated member extending from the base comprising a main body region and terminating in a piercing tip region and wherein the circumference of the tip region is substantially smaller than the circumference of the main body region and a shoulder region separates the main body region from the tip region;
an internal delivery channel formed by the hollow interior of the elongated member extending from the base to the tip and terminating in a discharge port at the piercing tip;
one or more inlet ports in the base and one or more conduits providing fluid communication between the one or more inlet ports and the internal channel;
wherein the difference in circumference of the tip region and the main body region is effective to form a non-contact drape region between the tip and the shoulder region on opposites sides of the tip when the tip is pressed into a flexible material;
wherein the main body of the elongated member has an elliptical cross-section in which the length of the major axis is 1.5 times the length of the minor axis, and further wherein the diameter of the tip region is less than 50% of the length of the major axis of the ellipse.

* * * * *